United States Patent [19]

Tan

[11] Patent Number: 5,320,113

[45] Date of Patent: Jun. 14, 1994

[54] INSTRUMENT FOR PROTECTING CORNEAL ENDOTHELIUM DURING CATARACT SURGERY

[76] Inventor: Ben G. Tan, 20924 Kelly Rd., Eastpointe, Mich. 48021

[21] Appl. No.: 41,153

[22] Filed: Apr. 1, 1993

[51] Int. Cl.$^5$ .............................................. A61B 17/00
[52] U.S. Cl. ......................................... 128/858; 606/1; 606/107
[58] Field of Search ................... 606/166, 167, 1, 107; 128/846, 20, 858

[56] References Cited

U.S. PATENT DOCUMENTS

| 4,732,150 | 3/1988 | Keener | 606/107 |
| 4,773,415 | 9/1988 | Tan | 606/107 |

FOREIGN PATENT DOCUMENTS

| 8300420 | 2/1983 | PCT Int'l Appl. | 128/20 |
| 1651894 | 5/1991 | U.S.S.R. | 606/166 |

Primary Examiner—Michael H. Thaler
Attorney, Agent, or Firm—John R. Benefiel

[57] ABSTRACT

An instrument and method for protecting the corneal endothelium during cataract removal surgery are described. The instrument includes wire legs having curved shielding sections held extending across the endothelium to prevent contact of the cataract nucleus during its removal. An angled tip formed by a wire loop connecting the legs contacts the endothelium and holds the shielding section away. The legs are compressed by squeezing together a pair of leg extensions having pads at the ends to be inserted in a small corneal incision, and a locating section of each leg contacts the cornea surface to position and hold the instrument in position when the legs are released.

9 Claims, 2 Drawing Sheets

INSTRUMENT FOR PROTECTING CORNEAL ENDOTHELIUM DURING CATARACT SURGERY

BACKGROUND OF THE INVENTION

The present invention pertains to an instrument for protecting the corneal endothelium of the eye during cataract extraction by the small incision technique, commonly known as the Phacoemulsification or Phaco technique.

In recent years, two surgical techniques for removing a cataract from the eye are employed. The large incision technique and the small incision or Phaco technique.

In the large incision technique, a large incision (approximately 8-10 mm) almost half the circumference of the cornea is made, and the cataract is expressed or squeezed out of the eye manually. The advantage with this technique is that it is much easier to perform. The disadvantages are the longer time to recuperate and it also creates more astigmatism.

In the small incision or Phaco technique, a small incision, approximately 3 mm long is made on the superior margin of the cornea. An ultrasonic cutting tip is then inserted inside the eye to remove the cataract. The advantages with this technique are the stronger wound, faster recuperation, and less astigmatism. The main disadvantage is that it is more difficult to perform.

There are two main problems with the Phaco technique, the first problem is the danger of rupturing the lens posterior capsule. The second problem is the risk of damaging the corneal endothelium.

The present invention deals exclusively with the second problem, namely with providing protection of the corneal endothelium during Phacoemulsification.

A brief description of the anatomy of the eye is in order, here made with reference to FIG. 1. The front part of the eyeball is a clear transparent structure called the cornea 10. The back surface of the cornea 10 is lined with a single layer of very delicate non-regenerating cells called the endothelium 12. The endothelium 12 keeps the cornea 10 transparent. When a large area of the endothelium 12 is damaged, as during cataract surgery, the cornea 10 swells up and becomes cloudy or opaque. Seeing through a cloudy cornea is like seeing through a foggy or frosted windshield of a car, and hence vision is very poor.

Posterior to the cornea 10 is the iris 16, the colored part of the eye (brown, blue or green eyes). The opening in the enter of the iris is the pupil 14.

Behind the iris is the lens 18 of the eye. A normal lens is clear and transparent. When the lens 18 becomes cloudy or opaque, as in old age, it is called a cataract. In surgery, the cloudy cataract is removed and replaced with a clear artificial lens called an intraocular lens implant.

During surgery using the Phaco technique, the cataract nucleus 18A tends to float up and come in contact with the corneal endothelium, as it is being removed with the ultrasonic cutting tip 20 (FIG. 8). Everytime the cataract nucleus touches the delicate endothelium, it destroys some endothelial cells. When damage to the endothelium 12 is extensive, the cornea 10 becomes permanently cloudy. The eye will not have good, useful vision. The operation is a failure and additional surgery, i.e., a corneal transplant, is needed later.

The object of the present invention is to protect the endothelium from contact with the cataract nucleus 18A during Phaco technique surgery.

SUMMARY OF THE INVENTION

This and other objects of the present invention, which will become apparent upon reading of the following specification and claims, are achieved by the use of an instrument formed of fine diameter surgical steel wire. The wire consists of a pair of elongated divergent wire legs joined at one end with a curved loop segment forming a tip. The wire legs each have a series of angles and curves formed therein, including a curved shielding section adjacent the tip. The free ends of the wire legs consist of unconnected slightly bent diverging wire extension segments angled out from the shielding sections which are received in round rubber pads. The shielding sections are curved convexly outwardly in the direction of the extension segments.

During surgery, the tip end of the instrument is inserted into the eye through a small side incision, advanced across the pupil, to position the convexly curved shielding sections over the endothelium. The instrument does not come into contact with the corneal endothelium except with the tip end, since the tip end is angled towards the endothelium. This positions the curved intermediate shielding sections to be spaced slightly away from the endothelium. The curved shielding sections of the instrument wire legs serve to protect the endothelium against contact with the cataract nucleus.

The curved shielding sections are each joined to a leg extension by a locating section functioning to properly locate and hold the instrument in proper position once the instrument is inserted and the legs released.

Preferably, the instrument is disposable, i.e., designed for a single use, because of the delicacy of the wire lengths which could easily be deformed when used repeatedly.

During surgery, the pads on each leg extension are grasped between the thumb and index finger, and the wire legs pressed closer together. The tip is inserted into the eye through a small side incision and the instrument advanced to position the leg shielding sections across the endothelium. As soon as pads are released, the spring action of the wire legs enable the legs to separate and fit tightly in the incision wound, to also help keep the instrument in proper position inside the eye.

During Phaco technique surgery, as the cataract is being cut and removed by the ultrasonic tip, the cataract nucleus tends to float up, spin and bounce in the anterior chamber. The intermediate curved shielding segments extend over and complementary to the curved surface of the endothelium, but spaced away slightly, effectively shielding the endothelium, and preventing the cataract nucleus from coming into contact with the endothelium. At completion of the Phaco procedure, the pads are squeezed together again, bringing the wire legs together, and the instrument is then easily withdrawn. The easy insertion, withdrawal and stability inside the eye are features which make this instrument a very useful tool in the cataract surgery.

DETAILED DESCRIPTION

Figure 1:
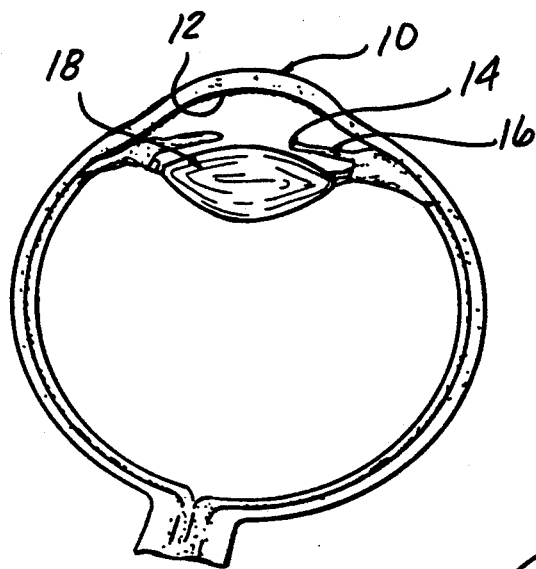
FIG. 1 is a sectional view of an eye showing the important parts involved in cataract surgery.
Figure 2:
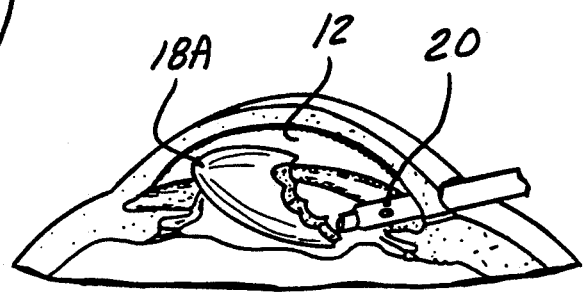
FIG. 2 is an enlarged sectional view of an eye on which the small incision Phacoemulsification technique cataract surgery is being performed
Figure 3:
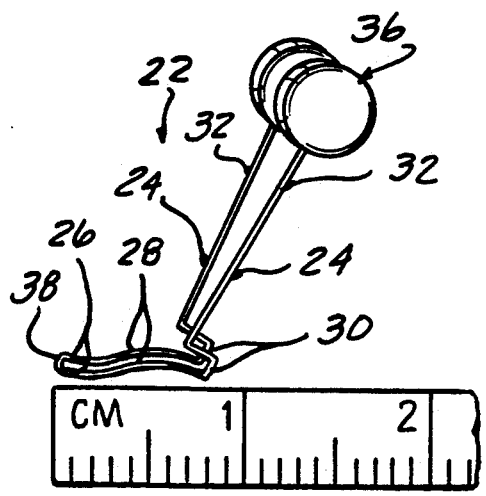
FIG. 3 is an enlarged perspective view of the instrument according to the present invention, with a reference scale.

In the following detailed description, certain specific terminology will be utilized for the sake of clarity and a particular embodiment described in accordance with the requirements of USC 112, but it is to understood that the same is not intended to be limiting and should not be so construed inasmuch as the invention is capable of taking many forms and variations within the scope of the appended claims. The measurements and angles given are only the averages for a typical instrument according to the present invention.

Referring to the drawings, and particularly FIGS. 3–6, the instrument 22 according to the present invention consists of a length of wire forming a pair of wire legs 24 joined at one end, diverging from each other in a general vee shape, each wire leg 24 shaped by a series of angles and curves. The instrument 22 is made of a fine diameter high quality steel wire, the diameter on the order of 0.2 mm.

Figure 6:
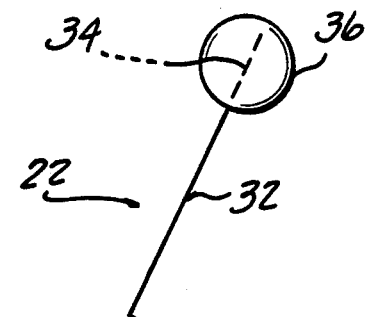
FIG. 6 is a side view of the instrument.
Figure 7:
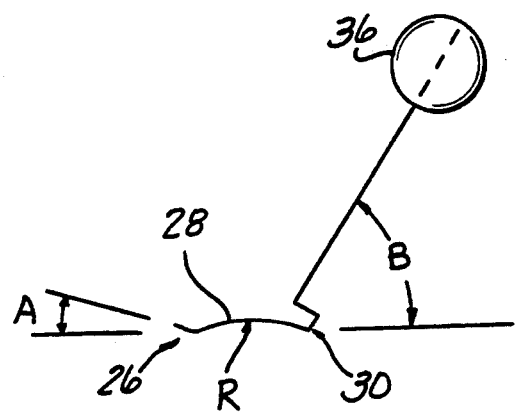
FIG. 7 is a side view of the instrument with the different angles and curves indicated.
Figure 8:
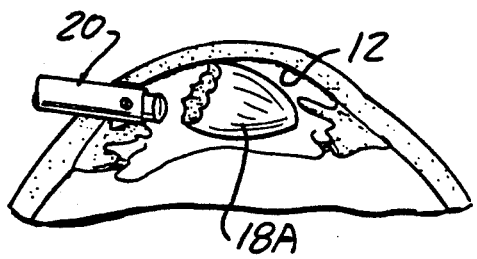
FIG. 8 is a sectional view of an eye on which Phacoemulsification is being performed without the use of the instrument according to the invention, showing the cataract nucleus coming in contact with the corneal endothelium.

Referring to FIG. 6, each leg 24 of the instrument 22 has a joined end 26, a curved shielding section 28, an angled locating section 30, and a slightly bent extension section 32. The joined ends 26 and the shielding sections 28 are the functional parts, for they are inserted inside the eye during surgery to provide protection to the endothelium 12.

The locating section 30 fits in the incision wound and provides fixation and stabilization for the instrument when in position. The leg extension sections 32 terminate in free ends 34 embedded in a round pad 36, here formed of silicone rubber discs 5 mm in diameter. The joined leg ends 26 forms a wire loop tip 1.5 mm long and 1 mm wide.

In the side view, the joined leg ends 26 are reversely bent from the curvature of the shielding sections 28 to make a slight upward angle A towards the leg extensions 32, in the embodiment shown here the angle A is equal to 14° from horizontally held shielding sections 28. This angle A locates the tip to create a clearance space between the shielding sections 28 and the corneal endothelium. Thus, only the wire loop tip 38 comes into contact with the endothelium.

The shielding sections 28 are of a length to approximate the distance across the endothelium, i.e., 7 mm long, and have a curvature which is convexly shaped out of the general plane defined by the shielding sections 28 of the legs 24 and towards the leg extension 32, the curvature approximating that of the endothelium, i.e, a radius curvature of 11.5 mm. As seen in FIGS. 3, 6, 7 and 9, each leg extension section 32 is located on the convex side of each shielding section 28.

Figure 9:
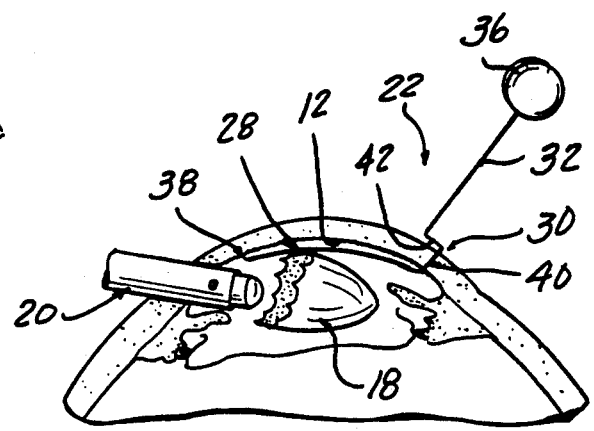
FIG. 9 is a sectional view of an eye on which Phacoemulsification is being performed with the instrument according to the invention in place.
Figure 10:
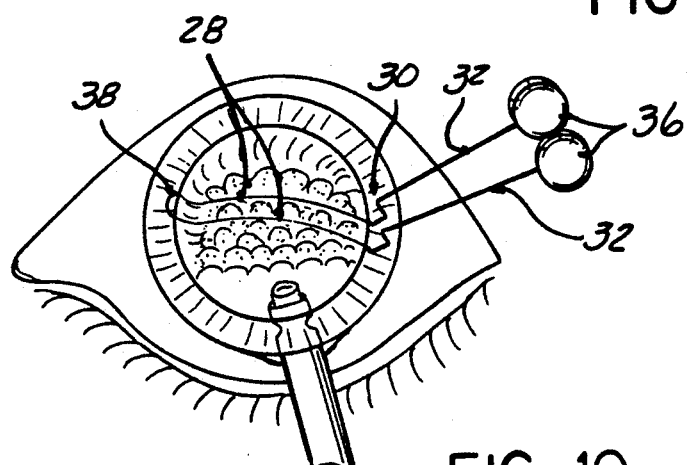
FIG. 10 is an inverted frontal view of an eye with instrument according to the invention in place during Phacoemulsification.

When placed inside the eye, the shielding sections 28 are curved complementary to but slightly spaced away from the endothelium, and act as a shield to prevent contact with the cataract nucleus as shown in FIG. 9.

The locating section 30 is comprised of a short outward segment 40 (FIG. 9) extending normally from each shielding section 28, slightly longer than the thickness of the cornea, i.e., 1.4 mm long, and short, i.e., 2.2 mm long, reverse segments 42, extending back over the shielding sections 28 to form a U-shape fit over the thickness of the cornea.

By contact with the perimeter of the short outward segments 40 act to properly limit the distance the instrument 10 is advanced into the eye.

The reverse segments 42 are drawn against the outer surface of the cornea when the legs 24 are released and spring-urged apart so that the right end of shielding sections 28 are positioned slightly spaced away and out of contact with the endothelium. This also holds the instrument 10 in position.

The leg extensions 32 extend at a major angle B, in the same direction as the convex curved shape of the shielding sections, angle B here equal to 85°, to position the pads 36 out of the way to avoid obstructing the view of the eye and provide a comfortable holding angle.

Figure 4:
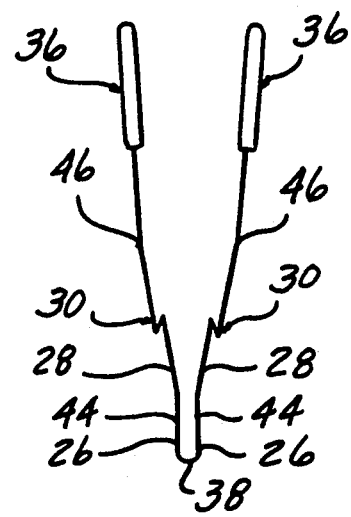
FIG. 4 is a plan view of the instrument, showing different angles.

As seen in the plan view of FIG. 4, each shielding section 28 has a slight (6°) divergent bend 44 which spreads the two legs 22 wider apart. At the midpoint of the extensions 32, there is a slight (8°) bend 46 which brings the legs 22 closer together, in a more parallel position.

Figure 5:
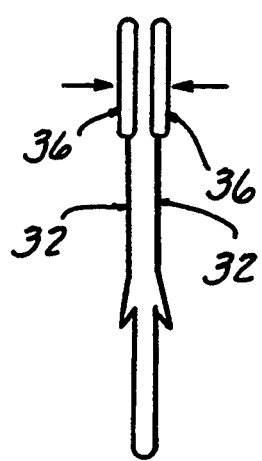
FIG. 5 is a plan view of the instrument showing the two wire legs drawn close together when the pads on the free ends of the leg extensions are squeezed.

During surgery the surgeon grasps the two pads 36 with his thumb and index finger, and the two wire legs are squeezed closer together as shown in FIG. 5. The separation between the legs 22 becomes much narrower, thereby making them possible to be inserted into the eye through a small side incision. When the shielding sections 28 of the instrument 10 are fully inserted in the eye as determined by contact with the outward segments 40, the surgeon releases the pads 36, and the two legs 22 spring wider apart. The spring action of the legs 22 causes the locating section 30 to be held to the eye helping keep the instrument 10 fit tightly in the wound with the shielding sections 28 in position extending over the endothelium.

At the completion of the surgery, the surgeon again squeezes the pads 36 together and gently pulls the instrument out of the eye. No suture is needed to close the small side incision.

I claim:

1. An instrument for shielding the corneal endothelium during eye surgery comprising:
   a pair of wire form legs joined at one end and free at the other end, said legs when relaxed diverging in a general vee shape,
   said joined ends forming a rounded tip at one end of said instrument;
   each leg formed with a shielding section adjacent said tip, said shielding sections each formed with a matching convexly curved shape extending out of the general plane of said shielding sections of said wire form legs and of a length so as to be able to extend across and match the corneal endothelium, approximately matching the curvature thereof;

said legs each angled at said tip reversely to said curved shape of said shielding sections to position said shielding sections complementary to but spaced away and out of contact with said endothelium with said tip in contact therewith; and each leg including an extension section connected to a said shielding section thereof and angled in the same direction as the convexly curved shape of said shielding section to enable emplacement and removal of said shielding sections after surgery is completed.

2. The instrument according to claim 1, each leg further including a locating section intermediate said shielding section and said extension section, said locating section including an outward segment extending transversely to said shielding section to limit the extent of insertion into an incision on one side of the cornea of the eye in order to properly locate said shielding section over the endothelium.

3. The instrument according to claim 2 wherein said locating section of each leg also includes a reverse segment connected to said outward segment and extending back in the direction of said respective shielding section to form a U-shape in combination with said associated outward segment and a portion of said shielding section, each of said reverse segments spaced from said respective shielding section a distance somewhat greater than the corneal thickness to thereby position the adjacent end of each shielding section slightly away from said endothelium with said reverse segments positioned against the outer surface of the cornea.

4. The instrument according to claim 3 wherein each outward segment is approximately 1.4 mm long.

5. The instrument according to claim 1 further including a pad affixed to the free end of each extension section.

6. The instrument according to claim 1 wherein each extension section is inclined at a substantial angle to said associated shielding section, said shielding section curved convexly towards said extension sections, said extension sections thereby positioned out of the way of the cornea when said instrument is in position during surgery.

7. The instrument according to claim 6 wherein each extension is slightly angled at an intermediate point to be less divergent from the other extension section.

8. The instrument according to claim wherein each shielding section is approximately 7 mm across.

9. The instrument according to claim 8 wherein each shielding section has a radius of curvature of approximately 11.5 mm.

* * * * *